(12) United States Patent  
Kasevich et al.

(10) Patent No.: US 6,275,738 B1
(45) Date of Patent: Aug. 14, 2001

(54) MICROWAVE DEVICES FOR MEDICAL HYPERTHERMIA, THERMOTHERAPY AND DIAGNOSIS

(75) Inventors: Raymond S. Kasevich, Mount Washington, MA (US); Stuart M. Selkowitz, Etna, NH (US)

(73) Assignee: KAI Technologies, Inc., Great Barrington, MA (US)

( * ) Notice: Subject to any disclaimer, the term of this patent is extended or adjusted under 35 U.S.C. 154(b) by 0 days.

(21) Appl. No.: 09/377,458

(22) Filed: Aug. 19, 1999

(51) Int. Cl.$^7$ .................................................. A61F 2/00
(52) U.S. Cl. .......................... 607/101; 607/102; 607/105
(58) Field of Search ............................. 607/96–105, 154, 607/156; 606/33

(56) References Cited

U.S. PATENT DOCUMENTS

| 4,601,296 | * | 7/1986 | Yerushalmi . | |
|---|---|---|---|---|
| 4,776,086 | | 10/1988 | Kasevich et al. . | |
| 4,823,812 | * | 4/1989 | Eshel et al. . | |
| 5,354,325 | | 10/1994 | Chive et al. . | |
| 5,431,648 | * | 7/1995 | Lev | 607/27 |
| 5,503,150 | | 4/1996 | Evans . | |
| 5,715,819 | | 2/1998 | Svenson et al. . | |
| 5,728,143 | | 3/1998 | Gough et al. . | |

FOREIGN PATENT DOCUMENTS

| 0 256 524 | 2/1988 | (EP) . |
|---|---|---|
| 0 783 903 | 7/1997 | (EP) . |
| WO 00/47283 | 8/2000 | (WO) . |

* cited by examiner

*Primary Examiner*—Roy Gibson
(74) *Attorney, Agent, or Firm*—Fish & Richardson P.C.

(57) ABSTRACT

To treat and diagnose tissue, a radiating antenna system is positioned within the tissue to radiate electromagnetic energy into a portion of the tissue desired to be heated, and a plurality of antenna elements are positioned for receiving and/or reflecting the radiated electromagnetic energy from the radiating antenna system. In certain applications, one or more of the antennas has an interior volume for receiving a heat exchange fluid to change the temperature of the tissue proximal to the receiving element.

54 Claims, 5 Drawing Sheets

MICROWAVE DEVICES FOR MEDICAL HYPERTHERMIA, THERMOTHERAPY AND DIAGNOSIS

BACKGROUND OF THE INVENTION

The present invention relates to microwave devices used in medical hyperthermia and thermotherapy (referred to collectively herein as "heat therapies") and diagnostics, and to methods of using such devices.

Localized heat therapies, i.e., hyperthermia (heating to temperatures below 45° C.) and thermotherapy (heating to temperatures above 45° C.), have been intensively investigated for the last two decades for many disease processes.

However, methods of delivering heat including warm fluid, focused ultrasound, radio frequency, and microwave approaches have been applied to abnormal tissue with only limited success. Because microwave energy can be applied with limited invasiveness, this approach is one that is currently being proposed.

For heat therapy to be applied safely, it is very important that the applied heat be confined to a target area alone, to avoid damaging nearby healthy tissue or organs.

Some devices for heat therapy have utilized microwave heating, for example, those disclosed in U.S. Pat. Nos. 4,700,716 and 4,776,086, the disclosures of which are incorporated herein by reference. Microwave energy elevates temperature by increasing the molecular motion within cell structures. As the frequency decreases, tissue penetration increases. Small diameter microwave antenna and other probes have been inserted into the body through normal body passages or, on occasion, directly into diseased tissue, using hollow plastic catheters.

SUMMARY OF THE INVENTION

The invention features a medical treatment system which utilizes microwave energy to provide heat treatment and diagnostic imaging of an arbitrarily shaped tissue mass. The term "microwave", as used herein, refers to electromagnetic energy in the microwave frequency spectrum of about 300 MHZ to about 300 GHz.

In one aspect of the invention, a medical treatment system for treatment of tissue includes a radiating antenna system, positioned to radiate electromagnetic energy through the tissue, and receiving elements, each configured to be positioned within or on the periphery of the tissue to receive at least a portion of the radiated electromagnetic energy from the radiating antenna system to the tissue. Each receiving element has an interior volume for receiving a heat exchange fluid to change the temperature of the tissue proximal to the receiving element.

In another aspect of the invention, a medical treatment system for treatment of tissue includes a radiating element system, positioned to radiate electromagnetic energy through the tissue, and reflecting elements, each configured to be positioned within or on the periphery of the tissue to reflect at least a portion of the radiated electromagnetic energy from the radiating antenna system to the tissue.

The inventions have numerous advantages. The radiated energy from the radiating antenna system is used to heat a desired area of tissue and the receiving elements are positioned to operate as "heat pipes", which act as a source or sink for the heated tissue. In addition, the individual receiving elements receive the radiated energy and provide signals which together provide an image and a property map of the area of tissue defined by the positioning of the elements.

Thus, the receiving elements improve control of the temperature of the volume of the tissue mass being radiated by the radiating antenna system. With this arrangement a safer, more efficacious delivery of microwave energy is provided. It is important to recognize that although the receiving elements serve as "heat pipes", in operation, they can provide both heating as well as cooling, depending on whether the fluid (e.g., liquid or gas) flowing through the heat pipe structure is hot or cold.

Embodiments of these aspects of the invention may include one or more of the following features.

At least one of the reflecting elements can include an interior volume for receiving a heat exchange fluid to change the temperature of the tissue proximal to the reflecting element.

One (or more) of the receiving and/or reflecting elements has a conduit for conveying the heat exchange fluid from a heat exchanger to a distal end of the receiving element. The receiving and/or reflecting element also has a transmission line extending from the distal end to a proximal end of the receiving and/or reflecting element. The conduit extends through the transmission line and forms a hollow center conductor of the transmission line. The transmission line also has an outer shield which is coaxial with respect to the conduit. The interior volume of the receiving and/or reflecting element and the conduit are sized to cause capillary action of fluid flowing between the internal volume and the conduit. The heat exchanger can include a condenser and the heat exchange fluid can be a coolant.

One or more of the receiving and/or reflecting elements has a temperature detector for sensing the temperature at a location proximate to that receiving element. In response to the sensed temperature, the detector provides signals for controlling the amount of fluid delivered to the interior volume of the receiving and/or reflecting element by the heat exchanger.

A measurement analyzer, connected to one (or more) of the receiving and/or reflecting elements, measures electrical characteristics associated with the receiving and/or reflecting element. These electrical characteristics include amplitude and phase voltage characteristics. The electrical characteristics can also be magnitude and phase of $S_{12}$ scattering parameter between the radiating antenna system and the receiving and/or reflecting element. A processor processes the measured electrical characteristic to generate an image of the tissue, and a display then displays the generated image.

One (or more) of the receiving and/or reflecting elements and the antenna system can be configured to deliver a material to the tissue. The material can be a chemotherapeutic agent, a heat sensitizer, or a cyropreservative.

At least one of the receiving elements includes a reflecting structure for reflecting the radiated electromagnetic energy from the radiating antenna system in a desired direction, thereby increasing the uniformity of the radiation applied to the targeted tissue.

The radiating antenna system has a plurality of antennas in the form of a collinear array. The radiating antenna system is configured to be received within the tissue to be treated.

A cannula is provided to receive the radiating antenna system within its inner lumen. The radiating antenna system includes antennas, each in the form of a collinear array.

The electromagnetic energy is radiated at a frequency in a range between 0.3 and 10 GHz, and at a power level in a range between about 100 mwatts and 150 watts.

In another aspect of the invention, a method of treating tissue is provided where a radiating antenna system is positioned within the tissue to radiate electromagnetic energy into a portion of the tissue desired to be heated, and receiving elements are positioned for receiving the radiated electromagnetic energy from the radiating antenna system with each receiving element positioned so that the path of received energy is through the portion of the tissue desired to be heated.

In still another aspect of the invention, a method of treating tissue is provided where a radiating antenna system is positioned within the tissue to radiate electromagnetic energy into a portion of the tissue desired to be heated, and reflecting elements are positioned for reflecting the radiated electromagnetic energy from the radiating antenna system toward the tissue to be treated.

With respect to these methods of treating tissue, the receiving and/or reflecting elements can be substantially positioned around a periphery of the portion of the tissue desired to be heated. The temperature proximate to at least one of the receiving and/or reflecting elements is sensed and, in response to the sensed temperature, the amount of fluid delivered to an interior volume of the receiving and/or reflecting elements is controlled.

Other features and advantages of the invention will be apparent from the drawings, the following Detailed Description, and the claims.

DETAILED DESCRIPTION

Figure 1:
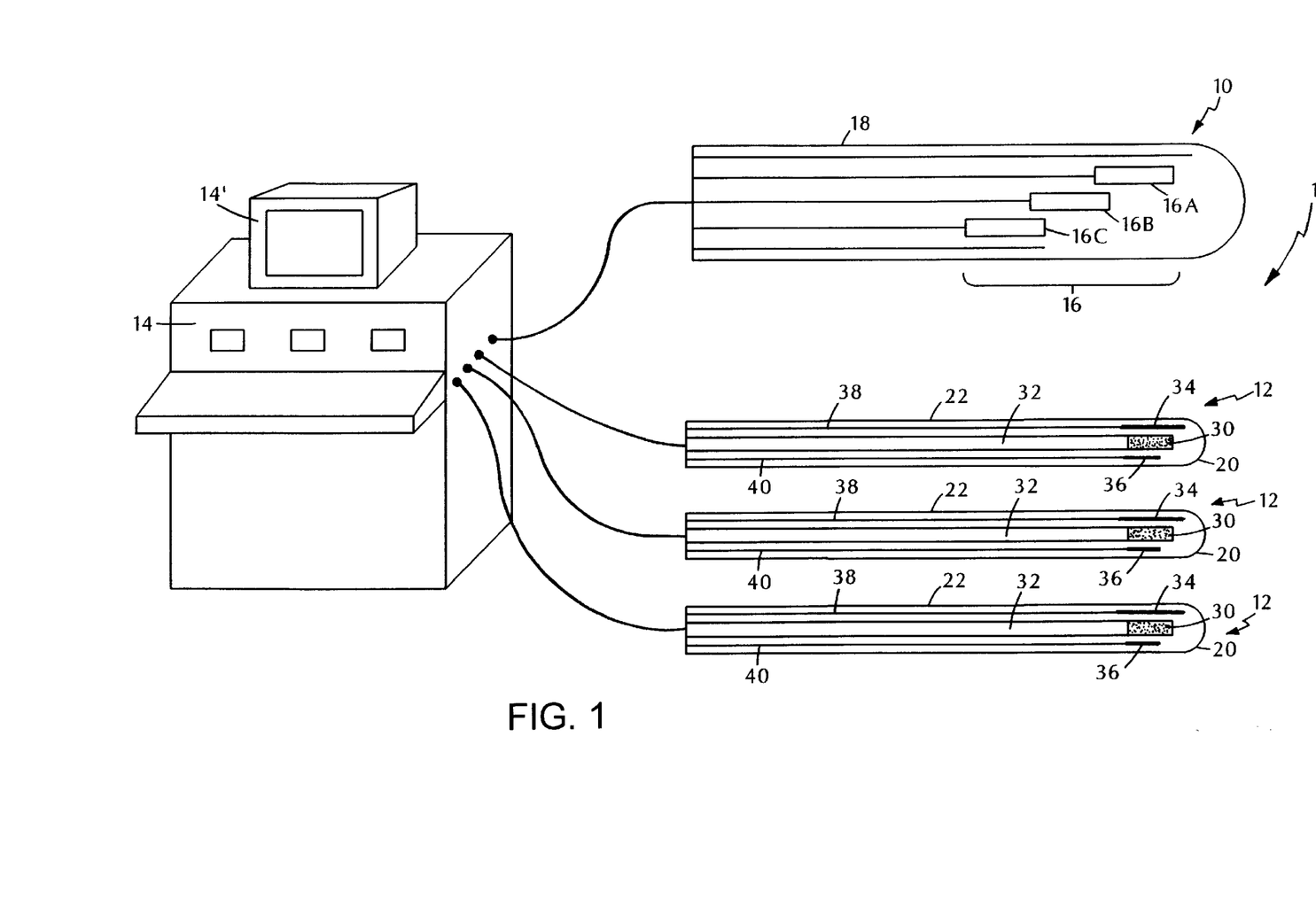
FIG. 1 is a schematic diagram of one embodiment of a tissue treatment and diagnosis system, showing three receiving microwave probes and one radiating microwave probe.

Referring to FIG. 1, microwave treatment and diagnosis system 1 includes at least one radiating microwave probe 10, at least two receiving microwave probes 12, a diagnosis and treatment station 14, and a monitor 14'. Receiving microwave probes 12 are configured and operated to act as "heat pipes." Hence, each one of receiving microwave probes 12 serves as a source or sink for thermal energy at the interface of that receiving microwave probe 12 and the adjacent tissue, resulting in a greater control of temperature at the interface. It is important to note that although receiving microwave probes 12 are said to act as heat pipes, receiving microwave probes 12 can cool as well as heat a targeted tissue. This allows for further control of temperature at the interface.

Figure 2:
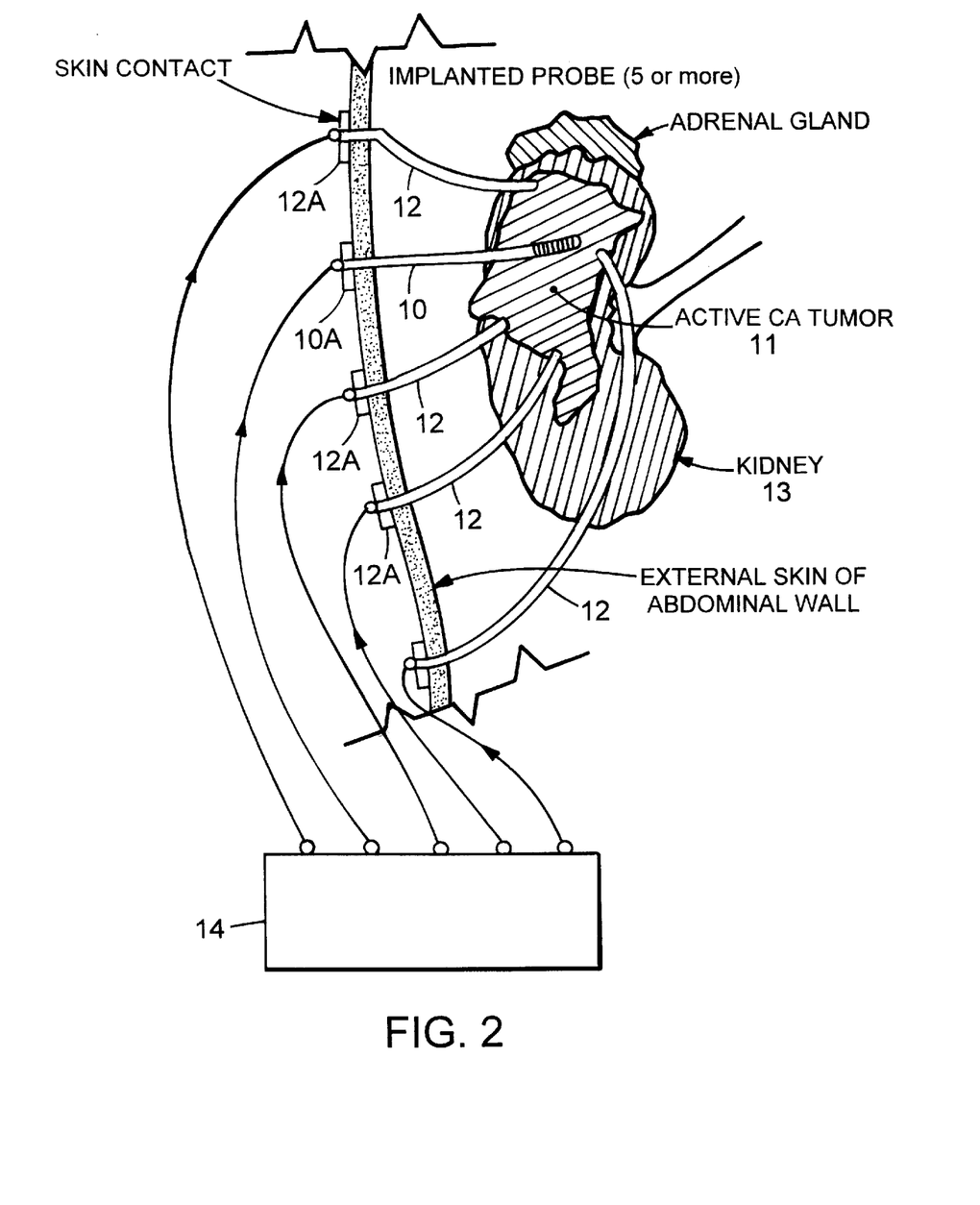
FIG. 2 is a diagrammatic view of the positions of the receiving microwave probes and the radiating microwave probe relative to a tissue mass under treatment.

Referring to FIG. 2, diagnosis and treatment station 1 allows diagnosing and applying heat therapy to a tissue mass 11 of arbitrary shape (here, a tumor in a patient's kidney 13). In particular, radiating microwave probe 10 and receiving microwave probes 12 are inserted into kidney 13 and positioned relative to one another so that electromagnetic energy travels through tissue mass 11 from radiating microwave probe 10 to receiving microwave probes 12. Therefore, as radiating microwave probe 10 radiates microwave electromagnetic energy, tissue mass 11 is heated. As can be seen in FIG. 2, radiating microwave probe 10 and receiving microwave probes 12 each extend to radiating probe contacts 10a and receiving probe contacts 12a, which, in use, are attached to the skin. Lead wires 15 connect probe contacts 10a, 12a to diagnosis and treatment station 14.

Receiving microwave probes 12 perform multiple functions. Because of their heat pipe structure, receiving microwave probes 12, under control of diagnosis and treatment station 14, act as heat sinks at the boundary of tissue mass 11. Hence, depending on their number and positioning relative to tissue mass 11, receiving microwave probes 12 can substantially limit heating to tissue mass 11. In effect, based on their positioning within the tissue, receiving microwave probes 12 can be used to define any arbitrary area within the tissue, and limit heat therapy substantially to that arbitrary area.

In addition, receiving microwave probes 12 act as antennas receiving radiated electromagnetic energy. Characteristics of the electromagnetic energy received at receiving microwave probes 12 depend on characteristics of tissue mass 11. Hence, for diagnosis, the characteristics of the received electromagnetic energy are measured by diagnosis and treatment station 14. Based on that measurement, diagnosis and treatment station 14 determines the characteristics of tissue mass 11 and can also generate an image of the tissue mass 11.

We will now describe in detail an embodiment of microwave treatment and diagnosis system 1. Referring to FIG. 1, each one of receiving microwave probes 12 includes a receiving antenna 20 deployed within a cannula 22. (The term "cannula" is intended to include all cannula-like structures, whether rigid or flexible, including catheters.) Receiving antenna 20 is configured not only to receive the microwave energy radiated by radiating microwave probe 10. Cannula 22 is constructed to be inserted into a portion of the body, typically through a body opening or passage, a small incision, or by using an internal stylet, as will be described in detail below. Receiving microwave probes 12 are preferably sized to have a diameter of 5–16 French (F.) and a length of approximately 1–18 cm.

Figure 3:
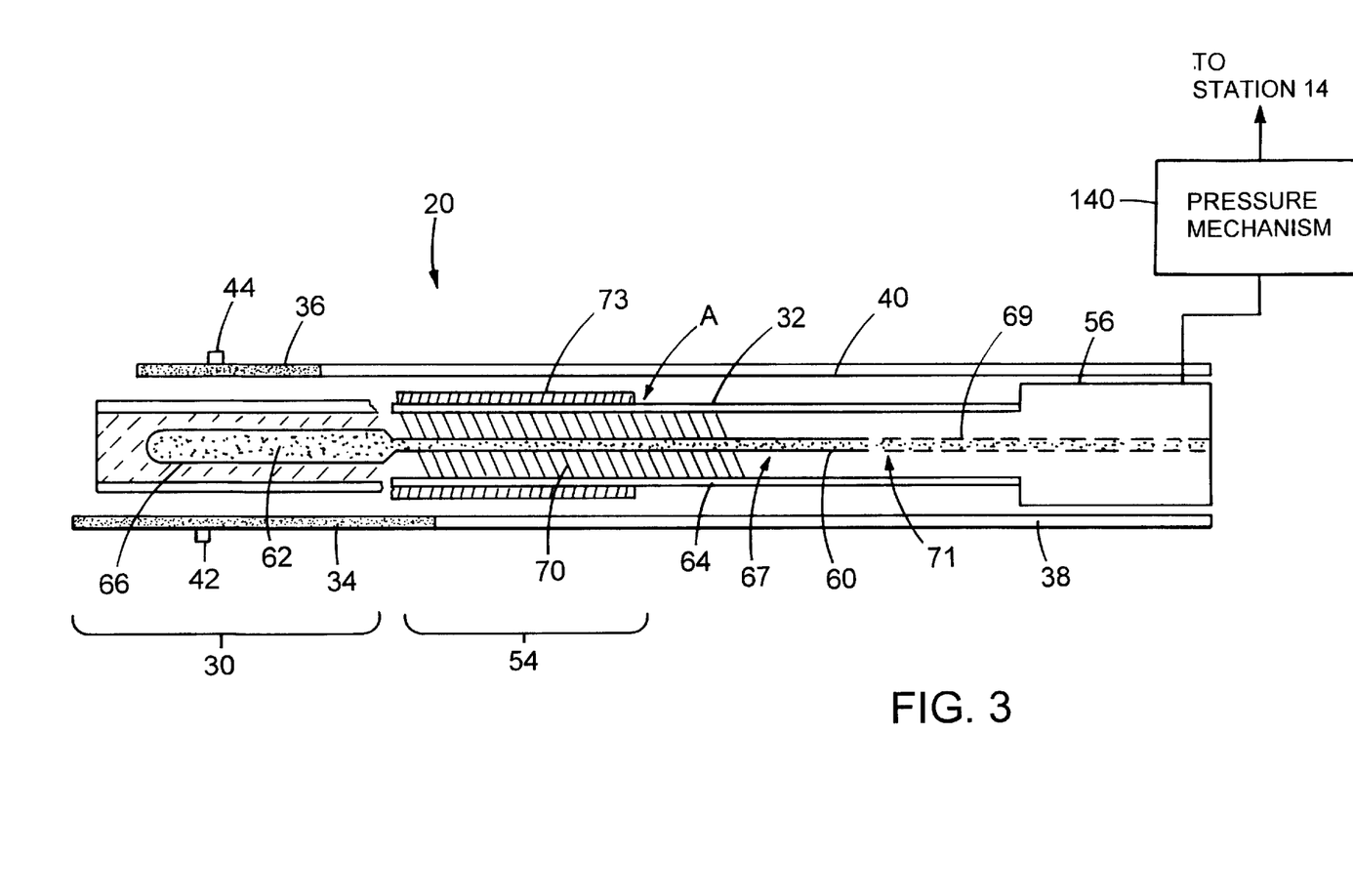
FIG. 3 is a cross-sectional side view of a receiving antenna of one of the receiving microwave probes.

FIG. 3 shows a detailed diagram of the structure of receiving antenna 20. Receiving antenna 20 includes an antenna portion 30 connected via a coaxial transmission line 32 to diagnosis and treatment station 14.

Antenna 20 further includes an RF reflector 34 and an RF director 36, located at the end of dielectric members 38 and 40, respectively. RF reflector 34 and RF director 36 are constructed by forming a metallic coating on dielectric members 38 and 40. RF reflector 34 and RF director 36 serve to improve the gain of antenna portion 30 by forming a three element Yagi array. The length of RF reflector 34 is generally commensurate with, or longer than, the length of antenna portion 30, while the length of director 36 is generally shorter (e.g., 75% of antenna length).

Reflector 34, in addition to increasing the gain of antenna portion 30, reflects microwave electromagnetic energy from radiating microwave probe 10 back towards the tissue. Reflector 34 can be differently shaped, such as having semi-cylindrical shape, to better reflect microwave electromagnetic energy back towards the tissue.

Thus, with their reflectors and directors, each one of receiving microwave probes 12 reflect the radiated energy back towards tissue mass 11. In combination, all of the receiving microwave probes 12 cause multiple reflections within tissue mass 11. The result of the multiple reflections is similar to a result of a microwave resonant cavity i.e., the multiple reflections increase the uniformity of the heat applied to the tissue mass.

Receiving antenna 20 is shown in FIG. 3 as being configured for providing heat pipe temperature control. Receiving antenna 20 includes antenna portion 30, a heat exchanger 56 and a flexible RF coaxial transmission line 32 connecting antenna portion 30 to diagnosis and treatment station 14. Antenna portion 30 is formed by a hollow conductive pipe 60 and a dielectric sheath 70 extending substantially the entire length of the conductive pipe. Conductive pipe 60 is one part of coaxial transmission line 32 for transmitting energy from antenna portion 30 to diagnosis and treatment station 14. At diagnosis and treatment station 14, antenna portion 30 can be selectively either grounded or open circuited.

When used as a heat pipe, conductive pipe 60 also functions as a capillary wick for a liquid or gas 62 passing therethrough. The capillary action is accomplished by having a relatively larger diameter portion 66 at antenna portion 30 to provide evaporative cooling, and a relatively smaller diameter "wick" portion 67 extending between portion 66 and heat exchanger 56. Larger diameter portion 66 is approximately $\lambda/2$ in length. At a junction 71, wick portion 67 extends beyond transmission line 32 to the heat exchanger 56 in the form of a dielectric tube 69.

When used in applications where cooling is required, heat exchanger 56 acts as a condenser having a refrigerant (e.g., cryogenic fluid). A pressure mechanism 140 under the control of diagnosis and treatment station 14 is used to control the amount and rate at which the fluid is delivered to antenna portion 30.

Receiving antenna 20 also includes several temperature sensors positioned at various points within receiving antenna 20. In particular, a temperature sensor 42 is placed on RF reflector 34. Another temperature sensor 44 is placed on RF director 36. Other temperature sensors (not shown) can also be placed along the walls of receiving antenna 20 or cannula 22. Sensors 42–44, and the other temperature sensors in receiving antenna 20, can be in the form of fiber optic sensors surrounded by a dielectric outer envelope. One example of a fiber optic sensor of this type is described in U.S. Pat. No. 4,700,716.

Antenna portion 30, RF reflector 34, and RF director 36 are fixed in position by potting them in a solid material within a tube (not shown), for example, by placing them in a tube and filling the tube with liquid, hardenable TEFLON® polymer. The tube can then be easily inserted into the cannula 22 for use by a physician.

Receiving antenna 20 also includes a transformer 54 provided by the combination of conductive pipe 60, an outer conductive coaxial sheath 64, dielectric sheath 70, and a metallic cylinder 73. Outer conductive coaxial shield 64 surrounds dielectric sheath 70 and extends along the length of conductive pipe 60 until terminating at a point just before larger diameter portion 66. Metallic cylinder 73 is approximately one-quarter wavelength in length and covers outer conductive coaxial shield 64, thereby electrically shorting the pair of members at point A. This electrical short presents an effective open circuit (high impedance) along the transmission line one-quarter wavelength away from the short.

Transformer 54 minimizes the reflected power seen by receiving element 30. Equally important, transformer 54 also prevents leakage of antenna currents along the outside structure of antenna 20. By appropriate selection of operating parameters, transformer 54 can be designed to provide both a minimum reflection coefficient as well as minimum leakage within the same frequency range.

Having described receiving microwave probes 12, we will now describe in general terms radiating microwave probe 10. A detailed description of radiating antenna probe 10 can be found in U.S. patent application Ser. No. 09/248,165, filed Feb. 9, 1999, incorporated herein by reference (hereinafter, referred to as "the '165 application"). Referring back to FIG. 1, radiating microwave probe 10 includes a collinear antenna 16 having a set of radiating antennas 16A, 16B, 16C deployed within a cannula 18. Cannula 18 is constructed to be inserted into a portion of the body, typically through a body opening or passage, a small incision, or by using internal stylets. Cannula 18 is preferably sized to have a diameter of 1–3 mm and a length of 2–6 cm.

The amplitude and phase of the radiation from each one of radiating antennas 16A, 16B, 16C is independently controlled by diagnosis and treatment station 14, so that their respective electromagnetic fields constructively add within, and subtract outside, a targeted tissue mass With this approach, a radiation pattern with desired narrow beamwidth and direction provides relatively high temperature and a focused heating to the tissue mass. Additionally, radiating antennas 16A, 16B, 16C can also have a heat pipe structure similar to receiving microwave probes 12, thereby improving the temperature control at the interface of radiating microwave probe 10 with the targeted area. Radiating antennas 16A, 16B, 16C thereby can have the same structure as that shown in FIG. 3 for receiving element 30, except that antenna portion 30 would be optimized for transmission rather than reception.

Figure 4:
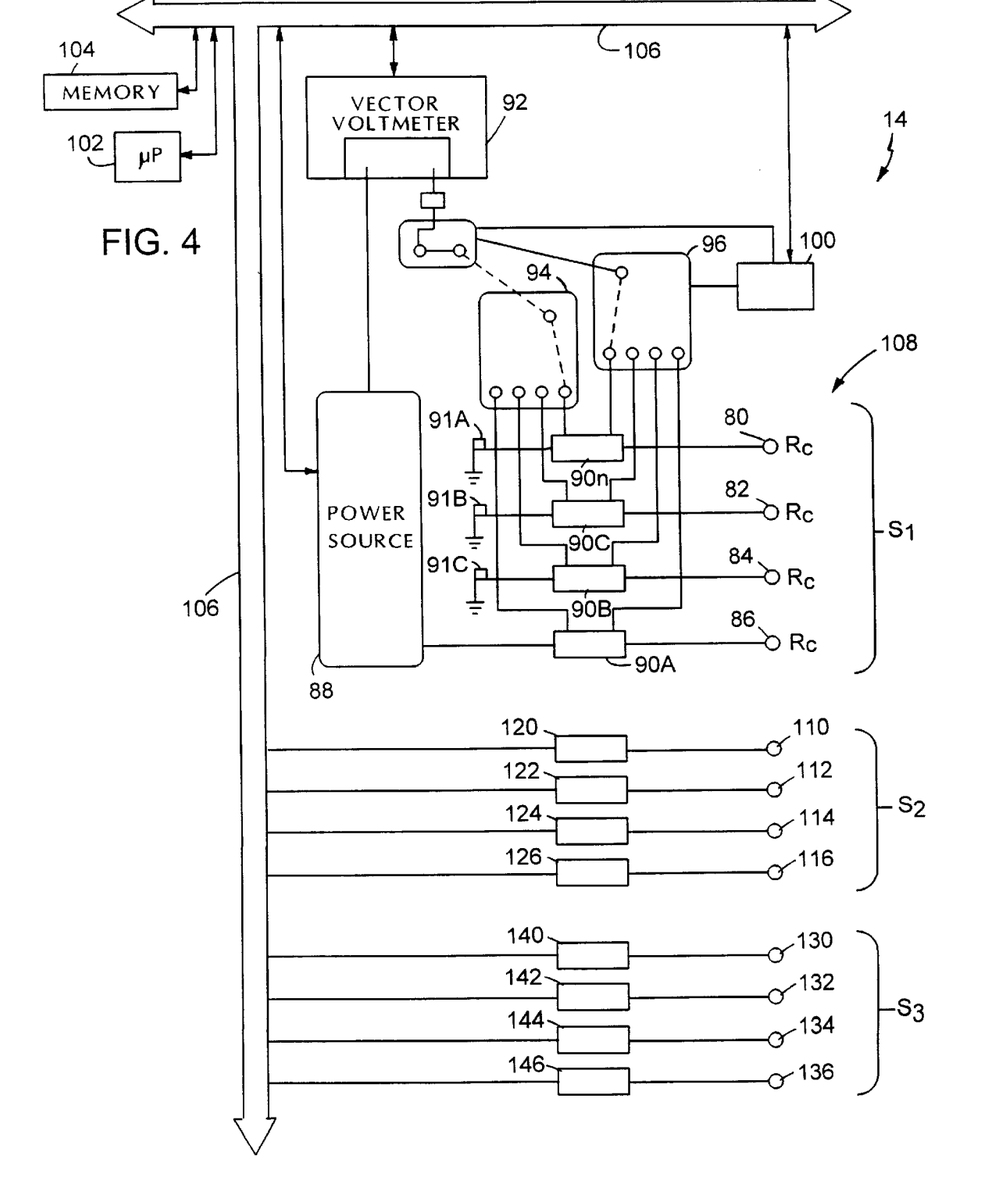
FIG. 4 is a schematic diagram showing the circuitry of a diagnosis and treatment station of tissue treatment and diagnosis system of FIG. 1.

Referring to FIG. 4, diagnosis and treatment station 14 includes a microprocessor 102, a memory unit 104, and a bus 106. Diagnosis and treatment station 14 also includes three subsystems for connection to radiating and receiving microwave probes 10 and 12. These subsystems are the power and measurement subsystems S1, temperature control units S2, and pressure mechanisms S3. Each of these subsystems are connected to bus 106 and are under control of application programs stored in memory unit 104 and executed by microprocessor 102. These subsystems will be shown and described as having connections for four devices, although other embodiments can include more connections.

Power and measurement subsystems S1 include an output port 86 coupled to a microwave power source 88 capable of, for example, providing approximately 5–25 watts of continuous wave power at 915 MHZ or 2450 MHZ to radiating microwave probe 10. Port 86 is coupled to power source 88 through a bidirectional coupler 90A. A fraction (e.g., 20 dB) of the microwave power source 80 is tapped from couplers 90B, 90C, 90D and provided to vector voltmeter (or measurement analyzer) 92 through a sequence of rotary switches 94, 96, 98. Note that power source 88 is capable of driving antennas 16A, 16B, 16C of radiating microwave probe 10 independent of one another.

Power and measurement subsystems S1 also includes several input ports 80, 82, 84 for connection to receiving microwave probes 12. Input ports 80, 82, 84 are coupled to electronic switches 91A, 91B, 91C through bi-directional coupler 90B, 90C, 90D, respectively. A fraction (e.g., 20 dB) of the microwave energy received at each one of receiving microwave probes 12 is tapped from couplers 90B, 90C, 90D and provided to vector voltmeter 92 through rotary switches 94, 96, 98. A switch controller 100 is used to select one of ports 80, 82, 84, 86 being examined at any given time. A 30dB attenuator is connected at the output of rotary switch 98 to protect vector voltmeter 92 from excessive power levels. Electronic switches 91A, 91B, 91C, under control of application programs running on microprocessor 102, can either connect an antenna of a receiving microwave probe to ground or allow the antenna to be open circuited.

Temperature control units S2 include ports 110, 112, 114, 116, each of which is connected, respectively, to a dedicated temperature control unit 120, 122, 124, 126. Each one of temperature control units 120, 122, 124, 126 is connected to bus 106 and is under control of application programs running on microprocessor 102. Each one of ports 110, 112, 114, 116 is connected to temperature sensors in one of the receiving microwave probes 12 or radiating microwave probe 10. Temperature control units S2 provide signals to microprocessor 102 indicative of the temperature at the probes.

Pressure mechanisms S3 include ports 130, 132, 134, 136 for connection to conductive pipes 60 of receiving microwave probes 12. If one or more of antennas 16A, 16B, 16C of radiating microwave probe 10 are configured as a heat pipe, then those antennas can also be connected to one of ports 130, 132, 134, 136. Each one of ports 130, 132, 134, 136 is coupled to a dedicated pressure mechanism 140, 142, 144, 146, respectively. Each one of pressure mechanisms 140, 142, 144, 146 is in turn connected to bus 106 and is under control of application programs executed by microprocessor 102.

We will now describe the operation of microwave diagnosis and treatment system 1. Referring to FIGS. 1–4, briefly, during operation, radiating microwave probe 10 is positioned and operated within tissue to radiate microwave electromagnetic magnetic energy towards two or more receiving microwave probes 12 through a targeted area of the tissue. The radiated electromagnetic energy can have a frequency in a range between about 0.3 and 10 Ghz, and a power level in a range between about 1 mwatts and 150 watts. Preferably, the radiated electromagnetic energy has a frequency of 915 MHZ or 2450 MHZ, at a power level of about 5–25 watts. Microwave receiving probes 12 are positioned within the tissue to receive and reflect back toward the targeted area the radiated electromagnetic energy.

Diagnosis and treatment station 14 controls the heat treatment applied by radiating and receiving microwave probes 10 and 12, and performs tissue diagnostic and inquiry operations.

During heat treatment of a targeted area, in response to electrical signals from temperature control unit S2, diagnosis and treatment station 14 controls power source 88 of power and measurement analysis subsystems S1 to generate electrical signals with the appropriate amplitude and phase characteristics so that radiating microwave probe 10 provides a focused beam in the direction of the targeted area.

Additionally, based on the signals indicative of the temperatures at radiating and receiving microwave probes 10 and 12, diagnosis and treatment station 14 controls pressure mechanisms S3 to convey heating or cooling fluid within antenna portion 30 of receiving microwave probes 12 to allow rapid and precise adjustment of the temperature at the interface between the antenna portions 30 and surrounding material. Hence, diagnosis treatment station 14 regulates heat at the boundary of a targeted tissue mass to ensure that heating applied to the tissue is substantially limited to the targeted tissue mass. One technique for achieving increased control over the applied heat is to simultaneously apply heat and cold to the tissue. Further details concerning the thermodynamic operation of heat pipes suitable for use in antenna 20 are described in U.S. Pat. No. 5,591,162, entitled "Treatment Method Using a Micro Heat Pipe Catheter", which is incorporated herein by reference.

As stated above, diagnosis and treatment station 14 also performs diagnostic functions. To do so, vector voltmeter 92 intermittently between heat applications measures amplitude and phase of the voltage induced on the receiving microwave probes 12. Application programs running on microprocessor 102 use the results of these measurements to determine magnitude and phase of a $S_{12}$ scattering parameter between the electromagnetic energy radiated by radiating microwave probe 12. The measured value of the $S_{12}$ scattering parameter is directly related to physical and electrical properties of a portion of the targeted tissue mass lying between the two probes, including its density and water content, polarization qualities, electrolyte composition, reflectance, blood flow velocity, and changing electrical properties over time. Another parameter that can measured is the input impedance of the radiating probe 10.

The measured values can then be displayed to the user. These measured values, together with other measurements, such as variance in phase and magnitude of signals received at the various receiving microwave probes 12, can be used to construct an image of the tissue under examination using conventional microwave tomography techniques. One technique for doing so is to change the position of radiating microwave probe 10 in a predetermined manner and to measure the various parameters as the position of the probe changes. In addition, measurements at low power levels can be taken and then compared to measurements at higher power levels, the results indicating the change in characteristics of the tissue as the tissue is heated. Diagnosis and treatment station 14 can then use these measurements to construct an image of the tissue under examination.

It should be noted that, when one of receiving microwave probes 12 is not providing signal information with respect to the voltages induced at its antenna, that probe can be used to act substantially as a reflector by allowing the antenna to be open circuited, substantially as a heat pipe by grounding the antenna, or as both.

In addition, diagnosis and treatment station 14 can display continuous readings of temperature changes at boundaries of a simulated or an ultrasound image of the targeted tissue mass. A schematic template of the targeted tissue mass representing the anatomy can be displayed with superimposed different colors representing different temperature ranges at different regions of the targeted area. Similarly, real-time or pre-recorded fluoroscopy, CAT scan, MRI, or ultrasound images can be superimposed with different colors representing different temperature ranges at different regions of the targeted area. Thus, the therapist or surgeon is able to determine, in real time, the target site and the effectiveness in applying heat from the system. Monitor 14' can display the temperature detected by each of the sensors as a function of time and provide beginning and end points for the treatment.

Based on signals received from the sensors, diagnosis and treatment station 14 is capable of issuing warning messages to be displayed on monitor 14' when temperatures exceed predetermined threshold values. Diagnosis and treatment station 14 may also automatically shutdown power source 88 if, for example, the temperatures remain high for an unacceptable time period or if a fault is detected in the system. Diagnosis and treatment station 14 also includes memory for storing statistical data including patient information, current laboratory data, as well as all data collected during the procedure.

Figure 5A:
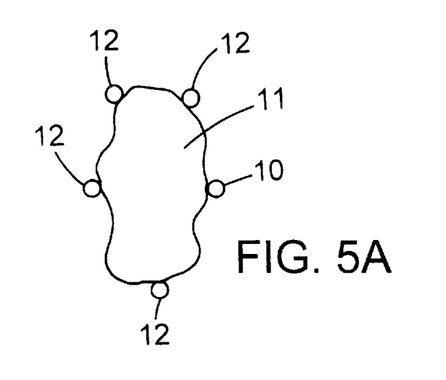
FIGS. 5A–5C are diagrammatic views of exemplary positions of the receiving probes and the radiating probe relative to different tissue masses under treatment.
Figure 5B:
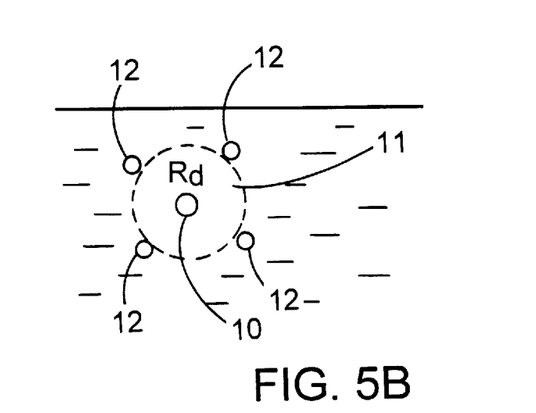
Figure 5C:
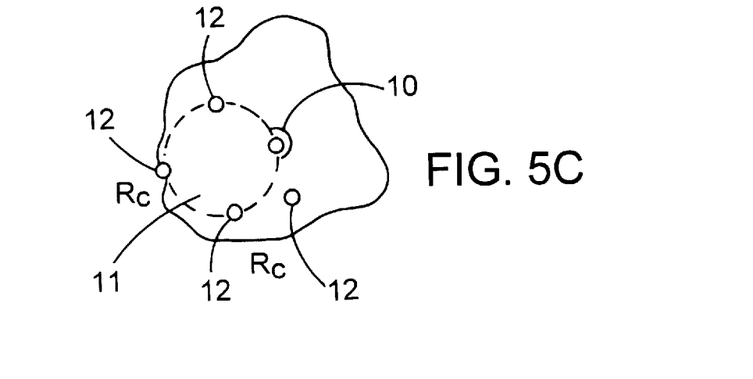

FIGS. 5A–5C show examples of manners in which radiating and receiving probes 10 and 12 can be positioned relative to one another and various targeted tissue areas 11. A physician can determine the optimum positioning based on the nature of the tissue to be treated, ease of access to that tissue, and the desired treatment. Note that broken lines in FIGS. 5B and 5C indicate targeted tissue masses defined by receiving microwave probes 12.

To position transmitting and receiving microwave probes 10, 12 within the body, various techniques may be used. For example, radiating and receiving microwave probes 10 and 12 can be positioned under the guidance of ultrasound, X-Ray, CAT scan, or fluoroscopy through natural body passages or openings, or small incisions, depending on the targeted tissue mass. In addition, endoscopes can be used to direct and/or deliver the probes to the targeted tissue mass. Alternatively, internal stylets can be used to deliver the probes. Radio-opaque internal stylets can be used to puncture the tissue and to enter into the patients body under guidance of guidance of ultrasound or fluoroscopy. After delivering the probes, the stylets can be removed.

Transmitting and receiving microwave probes 10, 12 can be used for various types of therapy. For example, transmitting and receiving microwave probes 10, 12 can be used to treat malignant and benign tumors, cysts, inflammatory conditions (hyperthermic low temperatures), rheumatic conditions and joint involvement (hyperthermic low temperatures), and muscle injuries. When treating cysts (such as hydrocoeles, spermatocoeles, or renal cysts), transmitting microwave probe 10 can be inserted into the cysts and heat the fluid therein to destroy the lining cells to reduce the mass of the cyst. Receiving microwave probes 12 can be located on the outside of the cysts to act as heat sinks and to reflect the microwave energy back toward the cyst.

Transmitting and receiving microwave probes 10, 12 can also be used to create a thrombus in an artery to occlude, for example, by inserting transmitting microwave probe 10 at a desired point and heating that point to cause localized clotting. Receiving microwave probes 12 enhance the localization of the applied heat. Transmitting and receiving microwave probes 10, 12 can also be used to locally heat infected tissue (e.g., cystitis or prostatitis) to destroy or hinder the infecting bacteria or viruses.

In body openings such as the bladder, transmitting microwave probe 10 can be inserted into the opening and receiving microwave probes 12 can be inserted to be located on the walls of the opening. The lining cells, which could be pathologic with a thin layer of widespread tumor, infection, or inflammation, can then be treated.

Transmitting and receiving microwave probes 10, 12 can be used for adjunctive therapies to increase effectiveness of other types of therapy such as chemotherapy and radiation therapy.

Other embodiments are within the scope of the claims.

For examples, receiving and transmitting microwave probes 10, 12 may be configured for delivering chemotherapeutic agents, heat sensitizers or cyropreservatives to the tissue. The delivered material can work synergistically with the microwave treatment. Chemotherapeutic agents may be better absorbed by heated tissue and tumor. Heat sensitizers allow to have an equivalent effect at a lesser power. Cyropreservatives allow a lower temperature to be attained before the tissue is destroyed by cellular ice crystallization.

In some embodiments of the receiving and transmitting microwave probes 10, 12 may be configured to not apply heat or cold to tissue adjoining portions of the probe. For example, one side of the heat pipe may be covered by insulating material so as to protect the tissue at that side of the probe. Such insulating material would then protect healthy tissue at one side of probe, while not affecting the heat or cold applied to the tissue to be treated.

In some embodiments, passive reflectors sized and configured to have contours of parts of the patient's body (e.g., breast or knee) may be used to enhance reflection and focusing microwave energy in parts of the body.

What is claimed is:

1. A medical system for treatment of tissue, the system comprising:
   a radiating antenna system positioned to radiate electromagnetic energy through the tissue; and
   a plurality of receiving elements, each configured to be positioned within or on the periphery of the tissue to receive the radiated electromagnetic energy from the radiating antenna system, each receiving element having an interior volume for receiving a heat exchange fluid to change the temperature of the tissue proximal to the receiving element.

2. The medical system of claim 1 wherein at least one of the receiving elements includes a conduit for conveying the heat exchange fluid from a heat exchanger to a distal end of said one of the receiving elements.

3. The medical system of claim 2 wherein at least one of receiving elements includes a transmission line extending from the distal end to a proximal end of said one of the receiving elements, the conduit extending through the transmission line.

4. The medical system of claim 3 wherein the conduit forms a hollow center conductor, and the transmission line further includes an outer shield disposed coaxially with respect to the conduit.

5. The medical system of claim 2 wherein the interior volume of said one of the receiving elements and the conduit are sized to cause capillary action of fluid flowing between the internal volume and the conduit.

6. The medical system of claim 2 further comprising the heat exchanger including a condenser and the heat exchange fluid is a coolant.

7. The medical system of claim 1 wherein at least one of the receiving elements includes a reflecting structure which reflects the radiated electromagnetic energy from the radiating antenna system into the tissue.

8. The medical system of claim 1 wherein the medical system further comprises a cannula having a proximal end, distal end, and an inner lumen extending therebetween, the cannula sized to receive the radiating antenna system.

9. The medical system of claim 1 wherein the radiating antenna system includes a plurality of antennas.

10. The medical system of claim 1 wherein the radiating antenna system is configured to be received within the tissue to be treated.

11. The medical system of claim 1 wherein at least one of the receiving elements includes a temperature detector for sensing the temperature at a location proximate to said one of the receiving elements and, in response to the sensed temperature, the detector provides signals for controlling the amount of fluid delivered to the interior volume of said one of the receiving elements by the heat exchanger.

12. The medical system of claim 1 further comprising a measurement analyzer, connected to at least one of the receiving elements, for measuring electrical characteristics associated with said one of the receiving elements.

13. The medical system of claim 12 wherein the electrical characteristics include amplitude and phase voltage characteristics.

14. The medical system of claim 12 further comprising
a processor processing the measured electrical characteristic to generate an image of the tissue, and
a display for displaying said image.

15. The medical system of claim 1 wherein at least one of the receiving elements and radiating antenna system is configured to deliver a material to the tissue.

16. The medical system of claim 15 wherein the material is a chemotherapeutic agent.

17. The medical system of claim 15 wherein the material is a heat sensitizer.

18. The medical system of claim 15 wherein the material is a cyropreservative.

19. The medical system of claim 1 wherein the electromagnetic energy has a frequency in a range between 0.3 and 10 GHz.

20. The medical system of claim 1 wherein the electromagnetic energy has a power level in a range between about 1 mwatts and 150 watts.

21. A method of treating tissue, comprising:
positioning a radiating antenna system to radiate electromagnetic energy into a portion of the tissue desired to be heated; and
positioning a plurality of antenna elements for receiving the radiated electromagnetic energy from the radiating antenna system, each receiving antenna element positioned so that the path of received energy is through the portion of the tissue desired to be heated.

22. The method of claim 21 further comprising positioning the receiving elements substantially around a periphery of the portion of the tissue desired to be heated.

23. The method of claim 21 further comprising providing within at least one of the receiving elements a reflecting structure for reflecting the radiated electromagnetic energy back to the portion of the tissue desired to be heated.

24. The method of claim 21 further comprising providing within each receiving element an interior volume for receiving a heat exchange fluid to change the temperature of the tissue desired to be heated and proximal to the receiving element.

25. The method of claim 24 further comprising providing, within at least one of the receiving elements, a conduit for conveying the heat exchange fluid from a heat exchanger to a distal end of said one of the receiving elements.

26. The method of claim 24 further comprising forming the interior volume of said one of the receiving elements and the conduit to cause capillary action of fluid flowing between the internal volume and the conduit.

27. The method of claim 24 further comprising:
sensing the temperature at a location proximate to at least one of the receiving elements; and
controlling, in response to the sensed temperature, the amount of fluid delivered to the interior volume of said one of the receiving elements.

28. The method of claim 24 further comprising receiving and measuring electrical signals from at least one of the receiving elements, the electrical signals providing an indication of the changing characteristics of the portion of the tissue desired to be heated.

29. The method of claim 28 wherein the electrical characteristics include amplitude and phase voltage characteristics.

30. The method of claim 21 further comprising delivering a material into the tissue.

31. The method of claim 30 wherein the material is a chemotherapeutic agent.

32. The method of claim 21 wherein radiating the electromagnetic energy is at a frequency in a range between 0.3 and 10 GHz.

33. The method of claim 21 wherein radiating the electromagnetic energy is at a power level in a range between about 1 mwatts and 150 watts.

34. A medical system for treatment of tissue, the system comprising:
a radiating antenna system positioned to radiate electromagnetic energy through the tissue; and
a plurality of reflecting elements, each configured to be positioned within or on the periphery of the tissue to reflect at least a portion of the radiated electromagnetic energy from the radiating antenna system to the tissue.

35. The medical system of claim 34 wherein at least one of the reflecting elements includes an interior volume for receiving a heat exchange fluid to change the temperature of the tissue proximal to the receiving element.

36. The medical system of claim 35 wherein said at least one of the reflecting elements having the interior volume includes a conduit for conveying the heat exchange fluid from a heat exchanger to a distal end of said at least one of the reflecting elements.

37. The medical system of claim 36 wherein said at least one of reflecting elements having the interior volume includes a transmission line extending from the distal end to a proximal end of the reflecting element, the conduit extending through the transmission line, the conduit forming a hollow center conductor, and the transmission line further including an outer shield disposed coaxially with respect to the conduit.

38. The medical system of claim 37 wherein the interior volume of said one of the reflecting elements and the conduit are sized to cause capillary action of fluid flowing between the internal volume and the conduit.

39. The medical system of claim 37 further comprising the heat exchanger including a condenser and the heat exchange fluid is a coolant.

40. The medical system of claim 35 wherein at least one of the reflecting antenna elements includes a temperature detector for sensing the temperature at a location proximate to said one of the reflecting elements and, in response to the sensed temperature, the detector provides signals for controlling the amount of fluid delivered to the interior volume of said one of the reflecting elements by the heat exchanger.

41. The medical system of claim 34 wherein at least one of the reflecting elements is configured to receive at least a portion of the radiated electromagnetic energy from the radiating antenna system the medical system further including a measurement analyzer, connected to said at least one reflecting element that receives radiated electromagnetic energy, the analyzer configured to measure electrical characteristics associated with the tissue.

42. The medical system of claim 41 wherein the electrical characteristics include amplitude and phase voltage characteristics.

43. The medical system of claim 41 further comprising
a processor which processes the measured electrical characteristic to generate an image of the tissue, and
a display to display said image of the tissue.

44. The medical system of claim 41 wherein at least one of the reflecting elements and radiating antenna system is configured to deliver a material to the tissue.

45. The medical system of claim 44 wherein the material is a chemotherapeutic agent.

46. The medical system of claim 34 wherein the medical system further comprises a cannula having a proximal end, distal end, and an inner lumen extending therebetween, the cannula sized to receive the radiating antenna system.

47. The medical system of claim 34 wherein the radiating antenna system includes a plurality of antennas in the form of a collinear array.

48. The medical system of claim 34 wherein the electromagnetic energy has a frequency in a range between 0.3 and 10 GHz and the electromagnetic energy has a power level in a range between about 1 mwatts and 150 watts.

49. A method of treating tissue, comprising:
    positioning a radiating antenna system to radiate electromagnetic energy into a portion of the tissue desired to be heated; and,
    positioning a plurality of reflecting elements to reflect at least a portion the radiated electromagnetic energy from the radiating antenna system toward the tissue desired to be heated.

50. The method of claim 49 further comprising positioning the reflecting elements substantially around a periphery of the portion of the tissue desired to be heated.

51. The method of claim 49 further comprising providing within each reflecting element an interior volume for receiving a heat exchange fluid to change the temperature of the tissue desired to be heated and proximal to the reflecting element.

52. The method of claim 51 further comprising providing within at least one of the reflecting elements a conduit for conveying the heat exchange fluid from a heat exchanger to a distal end of said one of the reflecting elements, the interior volume of said one of the reflecting elements and the conduit forward to cause capillary action of fluid flowing between the internal volume and the conduit.

53. The method of claim 51 further comprising:
    sensing the temperature at a location proximate to at least one of the reflecting elements; and
    controlling, in response to the sensed temperature, the amount of fluid delivered to the interior volume of said one of the reflecting elements.

54. The method of claim 49 wherein radiating the electromagnetic energy is at a frequency in a range between 0.3 and 10 GHz and has a power level in a range between about 1 mwatt and 150 watts.

* * * * *